United States Patent [19]

Wenger et al.

[11] Patent Number: 4,582,526
[45] Date of Patent: Apr. 15, 1986

[54] CARBAMIC ACID ESTER HERBICIDES

[75] Inventors: Jean Wenger, Uster; René Zurfluh, Bülach, both of Switzerland

[73] Assignee: Hoffmann-La Roche Inc., Nutley, N.J.

[21] Appl. No.: 559,652

[22] Filed: Dec. 9, 1983

[30] Foreign Application Priority Data

Dec. 17, 1982 [CH] Switzerland .......................... 7369/82
Sep. 21, 1983 [CH] Switzerland .......................... 5130/83

[51] Int. Cl.$^4$ ..................... A01N 43/60; A01N 43/40; A01N 43/42; C07D 241/44
[52] U.S. Cl. ........................................ 71/92; 544/354; 546/157; 546/300; 560/75; 560/150; 560/226; 560/229
[58] Field of Search ............................. 71/92; 544/354

[56] References Cited

U.S. PATENT DOCUMENTS 4,358,307 11/1982 Serban et al. ...................... 544/354

FOREIGN PATENT DOCUMENTS 23785 2/1981 European Pat. Off. .

*Primary Examiner*—Mark L. Berch
*Attorney, Agent, or Firm*—Jon S. Saxe; George M. Gould; John J. Maitner

[57] ABSTRACT

Carbamic acid ester compounds of the formula

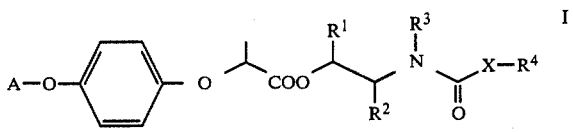

wherein A represents the group (a) or (b)

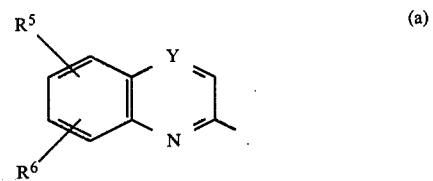

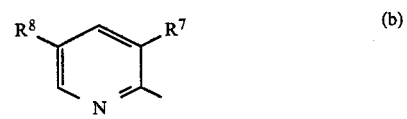

wherein $R^1$–$R^8$, X and Y are as defined hereinafter, processes for their preparation, herbicidal compositions containing these compounds and methods for the use of the compounds and the herbicidal compositions are disclosed.

22 Claims, No Drawings

CARBAMIC ACID ESTER HERBICIDES

SUMMARY OF THE INVENTION

The invention is directed to carbamic acid ester compounds of the formula

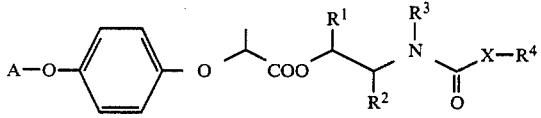

wherein A is the group (a) or (b)

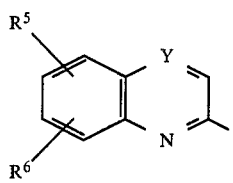

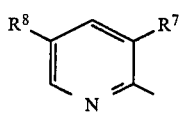

wherein $R^1-R^8$, X and Y are as defined hereinafter, and processes for their preparation. This invention is also directed to herbicidal compositions containing, as the active ingredient, a compound of formula I and methods for the use of these herbicidal compositions.

DETAILED DESCRIPTION OF THE INVENTION

The invention relates to carbamic acid ester compounds of the formula

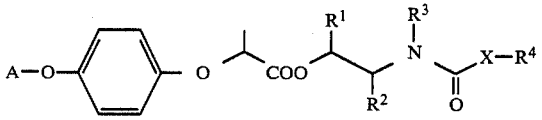

wherein A represents the group (a) or (b)

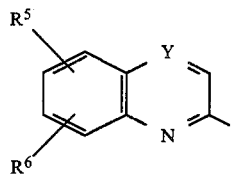

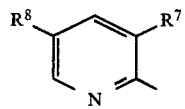

wherein $R^1$ is hydrogen, methyl or ethyl, $R^2$ is hydrogen, methyl or ethyl, $R^3$ is hydrogen or $C_{1-4}$-alkyl, $R^4$ is $C_{1-4}$-alkyl or halogen-substituted $C_{1-4}$-alkyl, $R^5$ is halogen. $C_{1-4}$-alkyl, halogen-substituted methyl. $C_{1-4}$-alkoxy or halogen-substituted methoxy. $R^6$ is hydrogen or chlorine, $R^7$ is hydrogen or chlorine, $R^8$ is chlorine or halogen-substituted methyl, X is oxygen or sulfur and Y is nitrogen or $—CH=$.

The invention is also directed to herbicidal compositions which contain, as the active ingredient, a compound of formula I, and methods for their use. The compounds have both preemergence and postemergence herbicidal activity.

In formula I the term "$C_{1-4}$-alkyl" encompasses both straight-chain and branched-chain alkyl groups such as methyl, ethyl, n-propyl, isopropyl, n-butyl, isobutyl and tert.butyl.

The term "halogen" encompasses fluorine, chlorine. bromine and iodine, with chlorine being preferred. The 2-chloroethyl group is a preferred halogen-substituted $C_{1-4}$-alkyl group.

The term "$C_{1-4}$-alkoxy" encompasses alkoxy groups in which the alkyl part corresponds to the above definition for $C_{1-4}$-alkyl.

The term "halogen-substituted methyl" encompasses preferably trifluoromethyl, difluoromethyl and difluorochloromethyl.

The term "halogen-substituted methoxy" encompasses preferably difluoromethoxy and trifluoromethoxy.

Preferred compounds of formula I are those wherein $R^2$ and $R^3$ are hydrogen, $R^4$ is methyl or ethyl, $R^5$ is fluorine, chlorine or trifluoromethyl, $R^6$ is hydrogen, $R^8$ is difluorochloromethyl or trifluoromethyl and X is oxygen.

Particularly preferred compounds of formula I are those in which A is a group of formula (a) and particularly those compounds in which Y is nitrogen, that is quinoxaline compounds of formula I(a). In the case o these quinoxaline compounds the D-form is especially preferred.

Representative compounds of formula I include:
S-ethyl 2-[[D-2-[p-[(6-chloro-1-quinoxalinyl)oxy]-phenoxy]propionyl]oxy]-N-methyl-ethylcarbamate.
methyl 2-[[D-2-[p-[(6-methyl-2-quinoxalinyl)oxy]-phenoxy]propionyl]oxy]ethylcarbamate.
methyl 2-[[D-2-[p-[6-(trifluoromethyl)-2-quinoxalinyl)oxy]phenoxy]propionyl]oxy]ethylcarbamate.
methyl 2-[[D-2-[p-[(6,7-dichloro-2-quinoxalinyl)oxy]-phenoxy]propionyl]oxy]ethylcarbamate.
S-ethyl 2-[[D-2-[p-[(6-chloro-2-quinoxalinyl)oxy]-phenoxy]propionyl]oxy]-N-methyl-ethylcarbamate.
methyl 2-[[D-2-[p-[(6-fluoro-2-quinoxalinyl)oxy]-phenoxy]propionyl]oxy]ethylcarbamate.
methyl 2-[[2-[p-[(6-chloro-2-quinolinyl)oxy]phenoxy]-propionyl]oxy]ethylcaramate.
methyl 2-[[2-[p-[(6-chloro-2-quinolinyl)oxy]phenoxy]-propionyl]oxy]propylcarbamate.
methyl 2-[[D-2-[p-[(6-chloro-2-quinolinyl)oxy]phenoxy]propionyl]oxy]ethylcarbamate.
methyl 2-[[D-2-[p-[(6-chloro-2-quinolinyl)oxy]phenoxy]propionyl]oxy]propylcarbamate,
ethyl 2-[[D-2-[p-[(6-bromo-2-quinolinyl)oxy]phenoxy]-propionyl]oxy]ethylcarbamate.
ethyl 2-[[D-2-[p-[(6-fluoro-2-quinolinyl)oxy]phenoxy]-propionyl]oxy]ethylcarbamate.
methyl 2-[[D-2-[p-[(6-fluoro--2-quinolinyl)oxy]phenoxy]propionyl]oxy]ethylcarbamate and
methyl 2-[[D-2-[p-[(6-fluoro-2-quinolinyl)oxy]phenoxy]propionyl]oxy]propylcarbamate.
Preferred compounds of formula I are:
Ethyl 2-[[D-2-[p-[(6-chloro-2-quinoxalinyl)oxy]phenoxy]propionyl]oxy]ethylcarbamate.

methyl 2-[[D-2-[p-[(6-chloro-2-quinoxlinyl)oxy]-phenoxy]propionyl]oxy]-N-methyl-ethylcarbamate.
ethyl 2-[[D-2-[p-[(6-chloro-2-quinoxalinyl)oxy]phenoxy]propionyl]oxy]-1-(ethyl)ethylcarbamate.
isobutyl 2-[[D-2-[p-[(6-chloro-2-quinoxalinyl)oxy]-phenoxy]propionyl]oxy]ethylcarbamate.
methyl 2-[[2-[p-[(6-chloro-2-quinoxalinyl)oxy]phenoxy]propionyl]oxy]ethylcarbamate.
ethyl 2-[[D-2-[p-[(6-fluoro-2-quinoxalinyl)oy]phenoxy]-proppionyl]oxy]ethylcarbamate and
methyl 2-[[D-2-[p-[(6-fluoro-2-quinoxalinyl)oxy]-phenoxy]propionyl]oxy]propylcarbamate.

Particularly preferred compounds of formula I are:
Methyl 2-[[D-2-[p-[(6-chloro-2-quinoxalinyl)oxy]-phenoxy]propionyl]oxy]ethylcarbamate.
methyl 2-[[D-2-[p-[(6-chloro-2-quinoxalinyl)oxy]-phenoxy]propionyl]oxy]propylcarbamate.
methyl 2-[[D-2-[p-[[5-(trifluoromethyl)-2-pyridyl]oxy]-phenoxy]propionyl]oxy]ethylcarbamate.
ethyl 2-[[D-2-[p-[[5-(trifluoromethyl)-2-pyridyl]oxy]-phenoxy]propionyl]oxy]ethylcarbamate and
methyl 2-[[D-2-[p-[[5-trifluoromethyl)-2-pyridyl]oxy]-phenoxy]prioionyl]oxy]propylcarbamate.

The compounds of formula I are prepared by one of the procedures described below.

(a) Reacting a substituted phenoxy-propionic acid of the formula

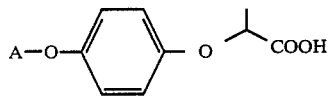
                           II wherein A is as described previously,
or a reactive derivative thereof, with a compound of the formula

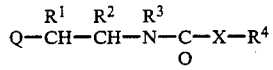
                           III $$Q-CH(R^1)-CH(R^2)-N(R^3)-C(=O)-X-R^4$$

wherein $R^1$, $R^2$, $R^3$, $R^4$ and X are as described previously and Q is a leaving group.

In accordance with this procedure a compound of formula II or a reactive derivative thereof is esterified with a compound of formula III. As the reactive derivative there is preferably used a salt, for example an alkali metal salt (e.g. the sodium, potassium or lithium salt), an alkaline earth metal salt (e.g. the magnesium, calcium or barium salt), a salt of an organic acid (e.g. a mono-, di- or trialkyl-ammonium salt or a pyridinium salt) or the ammonium salt.

The esterification of the acid of formula II or, preferably, a salt thereof, with the compound of formula III is conveniently carried out in an inert solvent and at a temperature of about −20° C. to 100° C. A temperature range between 0° C. and 40° C. is especially preferred. Inert organic solvents are preferably used as the solvent. Preferred solvents are ethers (e.g. diethyl ether and tetrahydrofuran), chlorinated hydrocarbons (e.g. dichloromethane and chloroform) and dimethylformamide.

When the free acid of formula II is used, the reaction is conveniently carried out in the presence of a base or an acid acceptor. For this purpose there can be used all conventional inorganic and organic acid binding agents preferably alkali metal and alkaline earth metal carbonates and bicarbonates and tertiary amines (e.g. triethylamine, dimethylaniline and pyridine).

The reactive derivative of the acid of formula II can also be a halide, imidazolide or anhydride, there being then used as the reaction partner a compound of formula III in which Q is hydroxy.

Also, the free acid of formula II can be reacted with a compound of formula III in which Q is hydroxy. The reaction is conveniently carried out in the presence of an acid catalyst or a condensing agent such as, for example, sulfuric acid, hydrochloric acid, p-toluene-sulfuric acid, dicyclohexylcarbodiimide or carbonyldiimidazole.

(b) Reacting a compound of the formula

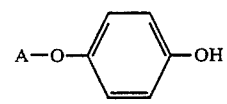
                           IV wherein A is as described previously,
or an alkali metal salt thereof, with a compound of the formula

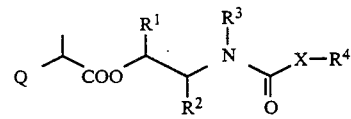
                           V wherein Q represents a leaving group and $R^1$, $R^2$, $R^3$, $R^4$ and X are as described previously, if required in the presence of a base.

(c) Reacting a compound of the formula

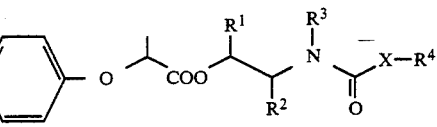
                           VI wherein $R^1$, $R^2$, $R^3$, $R^4$ and X are as described previously,
or an alkali metal salt thereof, with a compound of the formula
wherein A represents the group (a) or (b) above and Z is halogen, preferably chlorine or fluorine.

The term "leaving group" (Q) is preferably chlorine, bromine, iodine, mesyloxy or tosyloxy.

Procedures (b) or (c) can be carried out conveniently by reacting the phenol of formula IV or VI in the form of an alkali metal salt (e.g. the sodium salt) with a halide of formula V or VII. This is conveniently carried out in an aprotic solvent (e.g. dimethylformamide or dimethyl sulfoxide) or in pyridine at a temperature between about 50° C. and 150° C., preferably between 70° C. and 110° C.

The isolaton and purification of the compounds of formula I can be carried out according to conventional procedures well known in the art.

When in the manufacture of the compounds of formula I no planned synthesis for the production of pure optical isomers has been used (use of optically pure starting materials), the product normally occurs as the racemate. In this case the racemate can be separated into the isomers according to methods known per se.

When optically active starting materials are used there are obtained corresponding optically active products.

The starting materials of formulae II, IV and VII as well as reactive derivatives of the acids of formula II and alkali metal salts of the phenols of formula IV are either known or can be prepared according to methods well known in the art.

The starting materials of formulae III and V can be prepared in a manner known per se; for example, according to the following Reaction Scheme. In the Reaction Scheme the symbols $R^1$, $R^2$, $R^3$, $R^4$, X and Q are as described previously and Hal is a halogen atom, preferably chlorine or bromine.

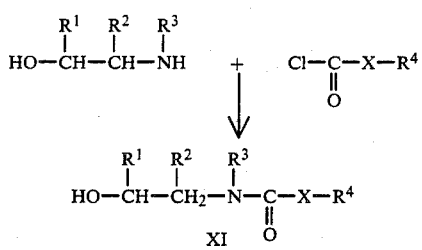

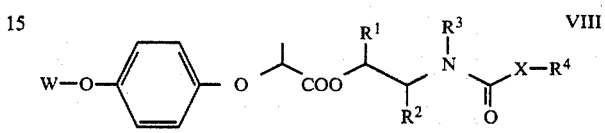

The starting materials of formula VI are novel and can be prepared by converting a compound of the formula

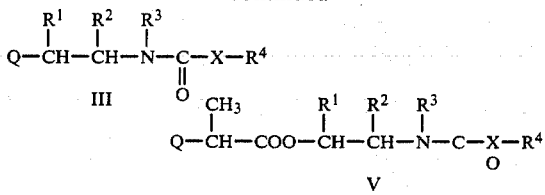

wherein $R^1$, $R^2$, $R^3$, $R^4$ and X are as described previously and W is a readily cleavable group, preferably benzyl.

with cleavage of W into a compound of formula VI.

The compounds of formula VIII can be prepared according to the following Reaction Scheme in which the symbols $R^1$, $R^2$, $R^3$, $R^4$, X, Q and W are as described previously.

Reaction Scheme

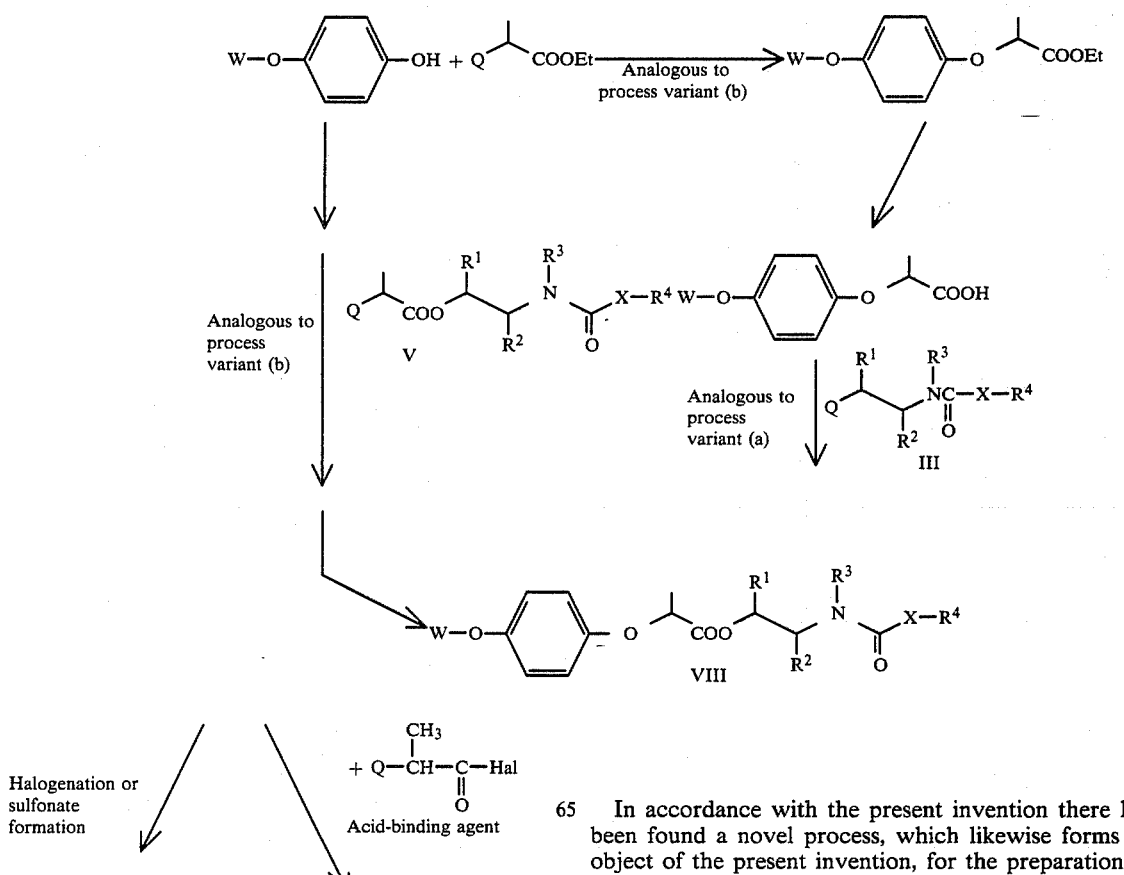

In accordance with the present invention there has been found a novel process, which likewise forms an object of the present invention, for the preparation of the 2-hydroxyqinoxalines of the formula

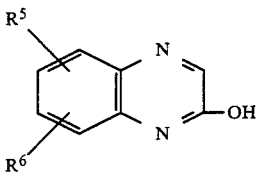

wherein $R^5$ and $R^6$ are as described previously, which are required for the preparation of the starting materials of formula VII wherein A represents group (a) in which Y is hydrogen, i.e. for the preparation of the starting materials of the formula

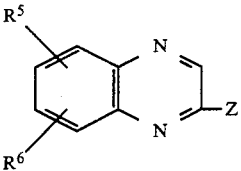

wherein Z is a halogen atom, preferably chlorine, and $R^5$ and $R^6$ are as described previously.

This process comprises reacting a compound of the formula

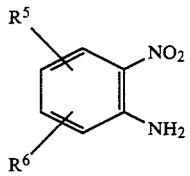

with a compound yielding the group of the formula

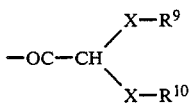

to give an amide of the formula

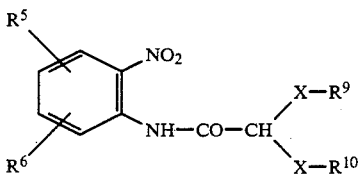

and, in optional sequence, reducing the nitro group in the compound of formula XII to the amino group and cleaving off the groups —X—$R^9$ and —X—$R^{10}$, whereby the compound of formula IX forms with ring closure.

In formulae X, XI and XII above the symbols $R^5$ and $R^6$ are as described previously, X is oxygen or sulfur and $R^9$ and $R^{10}$ independently of one another are $C_1$-$C_6$-alkyl, which is optionally substituted with halogen, lower alkoxy or lower alkylthio, or $C_2$-$C_4$-acyl (e.g. acetyl or propionyl). $R^9$ and $R^{10}$ together can also represent an alkylene group containing 2 or 3 carbon atoms.

The compound yielding the group of formula XI can be an ester, for example a lower alkyl ester (e.g. the ethyl ester) or a halide (e.g. the corresponding acid chloride) or another reactive derivative.

The reaction of a compound of formula X with a compound yielding the group of formula XI, for example the ethyl ester, is conveniently carried out according to the method described in Tetrahedron Letters 1971, pp. 321-22, namely by means of an alkali metal hydride (e.g. sodium hydride) in dimethyl sulfoxide, hexamethylphosphoramide, N-methyl-2-pyrrolidone, tetramethylurea, dimethylformamide or N,N-dimethylacetamide at a temperature between room temperature and the boiling point of the reaction mixture. Equimolar amounts of amine, ester and hydride are conveniently used.

Thereupon, in the compound of formula XII in optional sequence the nitro group is reduced to the amino group and the cleavage of the groups —X—$R^9$ and —X—$R^{10}$ is carried out. The reduction of the nitro group is conveniently carried out with hydrogen in the presence of a catalyst such as Raney-nickel, palladium or the like or with hydrazine, optionally in the form of the monohydrate, in the presence of ferric chloride or one of the above catalysts. This reduction can also be carried out by means of an alkali metal sulfide such as sodium sulfide or ammonium sulfide or an alkali metal dithionite (e.g. sodium dithionite). The reduction is conveniently carried out in a temperature range between about 0° C. and 30° C., preferably at about room temperature.

The amino compound obtained after reduction of the compound of formula XII and cleavage of the groups —X—$R^9$ and —X—$R^{10}$ cyclizes to the compound of formula IX. For the cleavage there is conveniently used an acidic catalyst, for example a Lewis acid (e.g. an acidic ion exchanger such as, for example, Amberlyst 15 or Amberlite 120). Conveniently, this cleavage and the ring closure are carried out in an inert solvent which is miscible with water (e.g. alcohol, acetone or the like). The ring closure can be carried out at a temperature between room temperature and the reflux temperature of the reaction mixture, preferably at the latter.

The compound of formula IX can be converted by halogenation in a manner known per se into the quinoxaline compound of formula VII.

Where asymmetric carbon atoms are present in the molecule, the compounds of formula I can exist in optically active isomeric forms. The procedures for preparing the compounds of formula I normally produce the compounds as the racemate. The racemic compounds can be resolved into their optical isomers using known procedures. If desired the isomers can also be prepared by synthesis from corresponding optically active starting materials.

The compounds of formula I possess herbicidal activity and are useful for the control of grasses, especially Echinochloa crus-galli, Setaria faberii, Agropyron repens, Sorghum bicolor, Alopecurus myosuroides and Avena fatua in soya. sugar beet and cotton crops. The compounds in accordance with the invention are especially well suited for the control of grasses in soya crops.

In general, the compounds of formula I are effective as herbicides when applied at a concentration of about 0.0 to about 0.5 kg/ha with the preferred concentration range being from about 0.05 to about 0.2 kg/ha.

This invention is also directed to herbicidal compositions which comprise inert carrier material and, as the active ingredient, one or more compounds of formula I.

These herbicidal compositions suitably contain, as the inert carrier material, at least one of the following ingredients: solid carrier materials, solvents or dispersion media, tensides (wetting and emulsifying agents), dispersing agents (without tenside action) and stabilizers. The herbicidal compositions of this invention can be formulated in the usual forms, for example dusts, powders, granulates, solutions, emulsions, suspensions, emulsifiable concentrates, pastes, and the like.

The compounds of formula I are in general water-insoluble. Thus, the usual methods of formulation of insoluble materials can be employed. For example, the compounds can be mixed with solid carrier substances, dissolved or suspended in suitable solvents or dispersion media, if necessary using tensides as wetting or emulsifying agents and/or dispersing agents, diluting pre-prepared emulsifiable concentrates with solvents or dispersion media, etc.

Suitable solid carrier materials include natural mineral substances, such as chalk, dolomite, limestone, aluminas, and silicic acid and salts thereof, for example, siliceous earth, kaolin, bentonite, talc, attapulgite and montmorillonite; synthetic mineral substances, such as highly dispersible silicic acid, aluminium oxide and silicates; organic substances, such as cellulose, starch, urea and synthetic resins; and fertilizers, such as phosphates and nitrates. The solid carrier substances can be present as powders or as granulates.

Suitable solvents or dispersion media include aromatic hydrocarbons, such as benzene, toluene, xylenes and alkylnaphthalenes; chlorinated aromatic and chlorinated aliphatic hydrocarbons, such as chlorobenzenes, chloroethylenes and methylene chloride; aliphatic hydrocarbons, such as cyclohexane and paraffins, for example, petroleum fractions; alcohols, such as butanol and glycol, as well as their ethers and esters; ketones, such as acetone, methyl ethyl ketone, methyl isobutyl ketone and cyclohexanone; and strongly polar solvents or dispersion media such as dimethylformamide, N-methylpyrrolidone and dimethyl sulfoxide, whereby such solvents or dispersion media preferably have flash points of at least 30° C. and boiling points of at least 50° C., and water. Also included in the solvents or dispersion media which can be used in preparing the herbicidal compositions are the so-called liquified gaseous extenders or carrier substances, these being products which are gaseous at room temperature and under normal pressure. Examples of such products are aerosol propellant gases such as halogenated hydrocarbons, for example, dichlorodifluoromethane. If a weed control composition in accordance with the invention is present in the form of a pressurized pack, then a solvent is conveniently used in addition to the propellant gas.

Tensides (wetting and emulsifying agents) suitable for use with the compounds of this invention can be anionic, cationic or nonionic.

Examples of anionic tensides include soaps; fatty sulfate esters, such as dodecyl sodium sulfate, octadecyl sodium sulfate and cetyl sodium sulfate; alkyl sulfonates, aryl sulfonates and fatty-aromatic sulfonates, such as alkylbenzene-sulfonates, for example, calcium dodecylbenzene sulfonate, and butylnaphthalene-sulfonates; and the more complex fatty sulfonates, such as the amide condensation products of oleic acid and N-methyltaurine or the sodium sulfonate of dioctyl succinate.

Examples of nonionic tensides include, for example, condensation products of fatty acids, fatty alcohols or fatty-substituted phenols with ethylene oxide; fatty acid esters and ethers of sugars of polyhydric alcohols; condensation products of sugars or polyhydric alcohols with ethylene oxide; block copolymers of ethylene oxide and propylene oxide, or alkyldimethylamine oxides.

Examples of cationic tensides include alkyldimethylbenzylammonium chlorides, dialkyldimethylammonium chlorides, alkyltrimethylammonium chlorides and ethoxylated quaternary ammonium chlorides.

Suitable dispersing agents (without tenside action) include lignin, sodium and ammonium salts of lignin sulphonic acids, sodium salts of maleic acid anhydride/diisobutylene copolymers, sodium and ammonium salts of sulphonated polycondensation products of naphthalene and formaldehyde, and sulphite lyes.

Dispersing agents which are especially suitable as thickening agents or antisettling agents include methylcellulose, carboxymethylcellulose, hydroxyethylcellulose, polyvinyl alcohol, alginates, caseinates and blood albumin.

Examples of suitable stabilizers are acid-binding agents, for example, epichlorohydrin, phenyl glycidyl ether, soya epoxides and the like; antioxidants, for example, gallic acid esters, butylhydroxytoluene and the like; UV-absorbers, for example, substituted benzophenones, diphenylacrylonitrile acid esters, cinnamic acid esters and the like; and deactivators, for example, salts of ethylenediaminotetraacetic acid, polyglycols and the like.

The herbicidal compositions of this invention can also contain, in addition to the compounds of formula I, synergistic agents and other active ingredients, such as insecticides, acaricides, bactericides, other herbicides, fungicides, plant growth regulators and fertilizers. Such combination preparations are suitable for increasing the activity or for broadening the spectrum of activity.

The herbicidal compositions of this invention generally contain between 0.005 and 95 percent by weight, preferably between 5 and 80 percent by weight, of one or more compounds of formula I as the active ingredient. The composition can be in the form of emulsifiable concentrates suitable for storage and shipment. In such concentrate formulations the active substance concentration is normally in the higher range, preferably between 10 and 80 percent by weight, especially between 25 and 75 percent by weight. These formulations can subsequently be diluted, for example, with the same or different inert ingredients, to give active ingredient concentrations which are suitable for practical use, i.e. preferably about 0.005 and 2 percent by weight, especially about 0.05 to 1 percent by weight. The active ingredient concentrations can, however, also be smaller or greater.

The herbicidal compositions of this invention can be prepared according to known formulation procedures.

For the preparation of pulverous preparations, the active ingredient, i.e. at least one compound of formula I, can be mixed with solid carrier materials, for example, by grinding the ingredients together, or the solid carrier material can be impregnated with a solution or suspension of the active ingredient and then the solvent or dispersion medium can be removed by evaporation, heating, or by vacuum under reduced pressure. By adding tensides or dispersing agents, such pulverous preparations can be made readily wettable with water, so that they can be converted into aqueous suspensions which are suitable, for example, as spray compositions.

The compounds to formula I can also be mixed with a tenside and a solid carrier material to form a wettable powder which is dispersible in water, or they can be mixed with a solid pre-granulated carrier material to form a granulate.

If desired, the compounds of formula I can be dissolved in a water-immiscible solvent, such as, for example, a high-boiling hydrocarbon, which conveniently contains a dissolved emulsifying agent, so that the solution becomes self-emulsifying upon addition to water. Alternatively, the active ingredient can be mixed with an emulsifying agent, and the mixture can then be diluted with water to the desired concentration. Moreover, the active ingredient can be dissolved in a solvent, and thereafter the solution can be mixed with an emulsifying agent. Such a mixture can likewise be diluted with water to the desired concentration. In this matter there are obtained emulsifiable concentrates or ready-for-use emulsions.

The use of the herbicidal compositions of this invention can be carried out according to usual application methods, such as sprinkling, spraying, dusting, pouring or scattering. The method of this invention for the control of weeds comprises treating the locus to be protected against weeds and/or the weeds with a compound of formula I or with a herbicidal composition in accordance with the invention.

The following Examples illustrate the invention in more detail:

I. MANUFACTURE OF THE ACTIVE SUBSTANCES OF FORMULA I

Example 1

56 g of D-2-[p-[(6-chloro-2-quinoxalinyl)oxy]phenoxy]propionic acid and 77.4 ml of thionyl chloride are heated at reflux together for 1.5 hours. The thionyl chloride is then distilled off under reduced pressure and the residue is dried in a high vacuum. To the residue containing the acid chloride formed are added 14 g of pyridine and 100 ml of methylene chloride and then dropwise at 5°–15° C. 23.6 g of methyl 2-hydroxypropylcarbamate dissolved in 50 ml of methylene chloride. The mixture is left to react at room temperature for 12 hours. The mixture is poured into water and extracted with ether. The extracts are washed with 2N sodium hydroxide, 2N hydrochloric acid, water and saturated sodium chloride solution, dried over sodium sulphate and concentrated on a rotary evaporator. By chromatography on silica gel with hexane/ether there is obtained pure methyl 2-[[D-2-[p-[(6-chloro-2-quinoxalinyl)oxy]phenoxy]propionyl]oxy]propylcarbamate; m.p. 94°–96° C., $[\alpha]_D^{22}$ +31.03° (c=0.93% in CHCl$_3$)

In an analogous manner there is obtained from (a) D-2-[p-[(6-chloro-2-quinoxalinyl)oxy]phenoxy]propionic acid and methyl 2-hydroxyethylcarbamate the methyl 2-[[D-2-[p-[(6-chloro-2-quinoxalinyl)oxy]phenoxy]propionyl]oxy]ethylcarbamate; m.p. 91°–94° C., $[\alpha]_D^{22}$ +28.84° (c=0.99% in CHCl$_3$).

ethyl 2-hydroxyethylcarbamate the ethyl 2-[[D-2-[p-[(6-chloro-2-quinoxalinyl)oxy]phenoxy]propionyl]oxy]ethylcarbamate; m.p. 96°–98° C., $[\alpha]_D^{22}$ +34.96° (c=0.39 in CHCl$_3$);

ethyl N-(2-hydroxyethyl)-N-methyl-thiolcarbamate the S-ethyl 2-[[D-2-[p-[(6-chloro-2-quinoxalinyl)oxy]phenoxy]propionyl]oxy]N-methyl-ethylcarbamate; $[\alpha]_D^{22}$ +25.43° (c=1.33% in CHCl$_3$), $n_D^{20}$ 1.5998.

methyl N-(2-hydroxyethyl)-N-methylcarbamate the methyl 2-[[D-2-[p-[(6-chloro-2-quinoxalinyl)oxy]phenoxy]propionyl]oxy]N-methyl-ethylcarbamate; $n_D^{20}$=1.5835, $[\alpha]_D^{22}$ +31.17° (c=0.75% in CHCl$_3$);

ethyl 1-ethyl-2-hydroxyethylcarbamate the ethyl 2-[[D-2-[p-[(6-chloro-2-quinoxalinyl)oxy]phenoxy]propionyl]oxy]1-(ethyl)ethylcarbamate; m.p. 71°–75° C., $[\alpha]_D^{22}$ +30.41° (c=0.91% in CHCl$_3$);

isobutyl 2-hydroxyethylcarbamate the isobutyl 2-[[D-2-[p-[(6-chloro-2-quinoxalinyl)oxy]phenoxy]propionyl]oxy]ethylcarbamate, m.p. 75°–78° C. $[\alpha]_D^{22}$ +31.77° (c=0.99% in CHCl$_3$);

(b) D-2-[p-[(6-fluoro-2-quinoxalinyl)oxy]phenoxy]propionic acid and methyl 2-hydroxyethylcarbamate the methyl 2-[[D-2-[p-[(6-fluoro-2-quinoxalinyl)oxy]phenoxy]propionyl]oxy]ethylcarbamate; m.p. 103°–106° C., $[\alpha]_D^{22}$ +33.08° (c=1.10% in CHCl$_3$);

(c) 2-[p-[(6-chloro-2-quinoxalinyl)oxy]phenoxy]propionic acid and methyl 2-hydroxyethylcarbamate the methyl 2-[[2-[p-[(6-chloro-2-quinoxalinyl)oxy]phenoxy]propionyl]oxy]ethylcarbamate; m.p. 103°–104.5° C.;

(d) 2-[p-[(6-chloro-2-quinolinyl)oxy]phenoxy]propionic acid and methyl 2-hydroxyethylcarbamate the methyl 2-[[2-[p-[(6-chloro-2-quinolinyl)oxy]phenoxy]propionyl]oxy]ethylcarbamate; m.p. 89°–90° C.;

methyl 2-hydroxypropylcarbamate the methyl 2-[[2-[p-[(6-chloro-2-quinolinyl)oxy]phenoxy]propionyl]oxy]propylcarbamate; NMR (60 MHz, CDCl$_3$) 1.25 ppm (2d, 3p), 1.65 ppm (d, 3p), 3.3 ppm (m, 2p), 3.6 ppm (2s, 3p), 4.8 ppm (q, 1p), 5.01 ppm (q, 1p), 6.7–8.1 ppm (9p);

(e) D-2-[p-[(6-chloro-2-quinolinyl)oxy]phenoxy]propionic acid and methyl 2-hydroxyethylcarbamate the methyl 2-[[D-2-[p-[(6-chloro-2-quinolinyl)oxy]phenoxy]propionyl]oxy]ethylcarbamate; m.p. 94°–97° C., $[\alpha]_D^{20}$ +30.176° (c=1.077% in CHCl$_3$);

methyl 2-hydroxypropylcarbamate the methyl 2-[[D-2-[p-[(6-chloro-2-quinolinyl)oxy]phenoxy]propionyl]oxy]propylcarbamate; m.p. 76°–78°, $[\alpha]_D^{20}$ +28.42° (c=1.05% in CHCl$_3$);

(f) D-2-[p-[(6-bromo-2-quinolinyl)oxy]phenoxy]propionic acid and ethyl 2-hydroxyethylcarbamate the ethyl 2-[[D-2-[p-[(6-bromo-2-quinolinyl)oxy]phenoxy]propionyl]oxy]ethylcarbamate; m.p. 68°–71° C., $[\alpha]_D^{20}$ +25.57° (c=0.7% in CHCl$_3$);

(g) D-2-[p-[(6-fluoro-2-quinolinyl)oxy]phenoxy]propionic acid and ethyl 2-hydroxyethylcarbamate the ethyl 2-[[D-2-[p-[(6-fluoro-2-quinolinyl)oxy]phenoxy]propionyl]oxy]ethylcarbamate; m.p. 95°–97°, $[\alpha]_D^{20}$ +31.003° (c=1.05% in CHCl$_3$);

methyl 2-hydroxyethylcarbamate the methyl 2-[[D-2-[p-[(6-fluoro-2-quinolinyl)oxy]phenoxy]propionyl]oxy]ethylcarbamate; m.p. 84°–86° C., $[\alpha]_D^{20}$ +31.07° (c=1.01% in CHCl$_3$);

methyl 2-hydroxypropylcarbamate the methyl 2-[[D-2-[p-[(6-fluoro-2-quinolinyl)oxy]phenoxy]propionyl]oxy]propylcarbamate; $[\alpha]_D^{20}$ +26.3° (c=1.0% in CHCl$_3$), NMR (60 MHz, CDCl$_3$) 1.25 ppm (2d, 3p), 1.67 ppm (d, 3p), 3.32 ppm (m, 2p), 3.65 ppm (2s, 3p), 4.80 ppm (q, 1p), 5.10 ppm (m, 1p), 6.8–8.2 ppm (9p);

(h) D-2-[p-[[5-trifluoromethyl)-2-pyridyl]oxy]phenoxy]propionic acid and methyl 2-hydroxyethylcarbamate the methyl 2-[[D-2-[p-[[5-trifluoromethyl)-2-pyridyl]oxy]phenoxy]propionyl]oxy]ethylcarbamate; $n_D^{20}=1.5022$, $[\alpha]_D^{22}$ +31.36° (c=1.03 in CHCl$_3$);

ethyl 2-hydroxyethylcarbamate the ethyl 2-[[D-2-[p-[[5-trifluoromethyl)-2-pyridyl]oxy]phenoxy]propionyl]oxy]ethylcarbamate; m.p. 63°–64° C., $[\alpha]_D^{22}$ +30.62° (c=0.96% in CHCl$_3$);

methyl 2-hydroxypropylcarbamate the methyl 2-[[D-2-[p-[[5-(trifluoromethyl)-2-pyridyl]oxy]phenoxy]propionyl]oxy]propylcarbamate; $[\alpha]_D^{20}$ +24.474° (c=1.08% in CHCl$_3$), $n_D^{20}=1.5043$;

(i) D-2-[p-[[5-(difluorochloromethyl)-2-pyridyl]oxy]phenoxy]propionic acid and methyl 2-hydroxyethylcarbamate the methyl 2-[[D-2-[p-[[5-(difluorochloromethyl)-2-pyridyl]oxy]phenoxy]propionyl]oxy]ethylcarbamate; $n_D^{20}=1.5292$, $[\alpha]_D^{20}$ +29.133° (c=0.99% in CHCl$_3$);

ethyl 2-hydroxyethylcarbamate the ethyl 2-[[D-2-[p-[[5-(difluorochloromethyl)-2-pyridyl]oxy]phenoxy]propionyl]oxy]ethylcarbamate: $n_D^{20}=1.5201$, $[\alpha]_D^{20}$ +27.77° (c=0.998% in CHCl$_3$);

methyl 2-hydroxypropylcarbamate the methyl 2-[[D-2-[p-[[5-(difluorochloromethyl)-2-pyridyl]oxy]phenoxy]priopionyl]oxy]propylcarbamate; $n_D^{20}=1.5127$, $[\alpha]_D^{20}$ +24.87° (c=1.046% in CHCl$_3$);

(k) 2-[p-[[(5-difluorochloromethyl)-2-pyridyl]oxy]phenoxy]propionic acid and methyl 2-hydroxyethylcarbamate the methyl 2-[[2-[p-[[(5-difluorochloromethyl)-2-pyridyl]oxy]phenoxy]propionyl]oxy]ethylcarbamate; 1H—NMR (CDCl$_3$, 60 MHz) 8.46 ppm (m,1H), 7.93 ppm (dd, 1H), 7.28–6.8 ppm (m, 5H), 5.13–4.73 ppm (m, 1H), 4.83 ppm (q, 1H), 4.30 ppm (t, 2H), 3.67 ppm (s, 3H), 3.57–3.23 ppm (m, 2H), 1.65 ppm (d, 3H);

2-[p-[[5-(trifluoromethyl)-2-pyridyl]oxy]phenoxy]propionic acid and methyl 2-hydroxyethylcarbamate the methyl 2-[[2-[p-[[5-(trifluoromethyl)-2-pyridyl]oxy]phenoxy]propionyl]oxy]ethylcarbamate; m.p. 56°–58.5° C.;

ethyl 2-hydroxyethylcarbamate the ethyl 2-[[2-[p-[[5-(trifluoromethyl)-2-pyridyl]oxy]phenoxy]propionyl]oxy]ethylcarbamate; 1H—NMR (CDCl$_3$, 60 MHz) 8.40 ppm (m,1H), 7.86 (dd, 1H), 7.20–6.80 ppm (m, 5H), 4.97–4.57 ppm (m, 1H), 4.80 ppm (q, 1H), 4.43–3.93 ppm (m, 4H), 3.57–3.23 ppm (m, 2H), 1.65 ppm (d, 3H), 1.22 ppm (t, 3H);

methyl 2-hydroxypropylcarbamate the methyl 2-[[2-[p-[[5-(trifluoromethyl)-2-pyridyl]oxy]phenoxy]propionyl]oxy]propylcarbamate; 1H—NMR (CDCl$_3$, 400 MHz) 8.41 ppm (m, 1H), 7.88 ppm (dd, 1H), 7.10–6.90 ppm (m, 5H), 5.10–5.0 ppm (m, 1H), 4.9–4.47 ppm (m, 2H), 3.66 and 3.61 ppm (2s, 3H), 3.46–3.09 ppm (m, 2H), 1.64 and 1.62 ppm (2d, 3H), 1.26 and 1.20 ppm (2d 3H);

ethyl 1-ethyl-2-hydroxyethylcarbamate the ethyl 2-[[2-[p-[[5-(trifluoromethyl)-2-pyridyl]oxy]phenoxy]propionyl]oxy]-1-(ethyl)ethylcarbamate; 1H—NMR (CDCl$_3$, 400 MHz) 8.42 ppm (m, 1H), 7.88 ppm (dd, 1H), 7.0–6.88 ppm (m, 5H), 4.79 ppm (2q, 1H), 4.64–4.43 ppm (m, 1H), 4.30–4.27 ppm (m, 1H), 4.17–4.01 ppm (m, 3H), 3.85–3.70 ppm (m, 1H), 1.64 and 1.63 ppm (2d, 3H), 1.55–1.30 ppm (m, 2H), 1.29–1.14 ppm (m, 3H), 0.91 and 0.89 ppm (2t, 3H);

methyl N-(2-hydroxyethyl)-N-methylcarbamate the methyl 2-[[-[p-[[5-(trifluoromethyl)-2-pyridyl]oxy]phenoxy]propionyl]oxy]-N-methyl-ethylcarbamate; 1H—NMR (CDCl$_3$, 60 MHz) 8.45 ppm (m, 1H), 7.91 ppm (dd, 1H), 7.25–6.8 ppm (m, 5H), 4.79 ppm (q, 1H), 4.32 ppm (t, 2H), 3.72 ppm (s, 3H), 3.55 ppm (t, 2H), 2.90 ppm (s, 3H), 1.62 ppm (d, 3H);

2-chloroethyl 2-hydroxyethylcarbamate the 2-chloroethyl 2-[[-[p-[[5-(trifluoromethyl)-2-pyridyl]oxy]phenoxy]propionyl]oxy]ethylcarbamate; 1H—NMR (CDCl$_3$, 60 MHz) 8.45 ppm (m, 1H), 7.92 ppm (dd, 1H), 7.25–6.80 ppm (m, 5H), 5.1–4.61 ppm (m, 2H), 4.5–4.17 ppm (m, 4H), 3.8–3.2 ppm (m, 4H), 1.65 ppm (d, 3H);

isopropyl 2-hydroxypropylcarbamate the isopropyl 2-[[2-[p-[[5-(trifluoromethyl)-2-pyridyl]oxy]phenoxy]propionyl]oxy]propylcarbamate; 1H—NMR (CDCl$_3$, 60 MHz) 8.46 ppm (m, 1H), 7.91 ppm (dd, 1H), 7.24–6.8 ppm (m, 5H), 5.26–4.45 ppm (m, 4H), 3.52–3.06 ppm (m, 2H), 1.63 ppm (d, 3H), 1.22 ppm (d, 9H);

isobutyl 2-hydroxyethylcarbamate the isobutyl 2-[[2-[p-[[5-(trifluoromethyl)-2-pyridyl]oxy]phenoxy]propionyl]oxy]ethylcarbamate; 1H—NMR (CDCl$_3$, 60 MHz) 8.45 ppm (m, 1H), 7.92 ppm (dd, 1H), 7.25–6.8 ppm (m, 5H), 4.82 ppm (q, 1H), 5.07–4.6 ppm (m, 1H), 4.29 ppm (t, 2H), 3.85 ppm (d, 2H), 3.58–3.23 ppm (m, 2H), 1.90 ppm (m, 1H), 1.65 ppm (d, 3H), 0.90 ppm (d, 6H);

butyl 2-hydroxyethylcarbamate the butyl 2-[[2-[p-[[5-(trifluoromethyl)-2-pyridyl]oxy]phenoxy]propionyl]oxy]ethylcarbamate; 1H—NMR (CDCl$_3$, 60 MHz) 8.45 ppm (m, 1H), 7.91 ppm (dd, 1H), 7.27–6.78 ppm (m, 5H), 5.03–4.6 ppm (m, 1H), 4.82 ppm (q, 1H), 4.52–3.92 ppm (m, 4H), 3.6–3.22 ppm (m, 2H), 1.9–1.1 ppm (m, 4H), 1.63 ppm (d, 3H), 0.93 ppm (t, 3H).

The isobutyl 2-hydroxyethylcarbamate used above as the starting material can be prepared as follows:

42.8 g of ethanolamine are placed in 350 ml of methylene chloride. 47.8 g of isobutyl chloroformate are then added dropwise during 1 hour at 5°–15° C. while cooling with ice. After stirring at room temperature for a further 4 hours, the methylene chloride is removed by evaporation and the residue is distilled. There is obtained pure isobutyl 2-hydroxyethylcarbamate; b.p. 111°–113° C./0.07 Torr.

Example 2

A mixture of 1.99 g of 2,6-dichloroquinoxaline, 2.83 g of methyl 2-[[2-(4-hydroxyphenoxy)propionyl]oxy]ethylcarbamate, 1.4 g of potassium carbonate and 20 ml of N,N-dimethylformamide is stirred at room temperature overnight. For the working-up, the mixture is poured on to ice-water and extracted with ethyl acetate. The extracts are washed with water and sodium chloride solution, dried over sodium sulphate and evaporated. By chromatography on silica gel with hexane/ethyl acetate (2:1) there is obtained pure methyl 2-[[2-p-[(6-chloro-2-quinoxalinyl)oxy]phenoxy]propionyl]oxy]ethylcarbamate; m.p. 103°–104.5° C.

In an analogous manner, from methyl 2-[[D-2-(4-hydroxyphenoxy)propionyl]oxy]ethylcarbamate there is obtained methyl 2-[[D-p-[(6-chloro-2-quinoxalinyl)oxy]phenoxy]propionyl]oxy]ethylcarbamate; m.p. 93°–95° C.

The methyl 2-[[2-(4-hydroxyphenoxy)propionyl]oxy]ethylcarbamate used above as the starting material can be prepared as follows:

9.0 g of methyl 2-hydroxyethylcarbamate and 6.7 g of pyridine are dissolved in 70 ml of diethyl ether and cooled to 0°–5° C. 18.0 g of 2-bromopropionyl bromide, dissolved in 20 ml of diethyl ether are now added dropwise within 30 minutes and the mixture is stirred at ice temperature for a further 30 minutes and at room temperature for 1 hour. For the working-up, the mixture is poured into water and extracted with diethyl ether. The ether phase is washed twice with sodium chloride solution, dried over anhydrous sodium sulphate and evaporated under reduced pressure. There is obtained methyl 2-(2-bromopropionyloxy)ethylcarbamate as a yellow oil which is used without further purification.

A mixture consisting of 2.8 g of hydroquinone monobenzyl ether, 3.56 g of methyl 2-(2-bromopropionyloxy)ethylcarbamate, 3.87 g of potassium carbonate and 30 ml of acetone is heated at reflux for 2 hours while stirring. The cooled mixture is filtered and the filtrate is evaporated. After flash chromatography, the residue gives pure methyl 2-[[2-(4-benzyloxyphenoxy)propionyl]oxy]ethylcarbamate of melting point 79°–81° C. 1.0 g thereof is dissolved in 100 ml of ethyl acetate and hydrogenated in the presence of 0.1 g of 5% palladium-on-carbon. After shaking for 45 minutes, the hydrogen uptake has finished. The catalyst is filtered off and the solvent is removed on a rotary evaporator. There is obtained methyl 2-[[2-(4-hydroxyphenoxy)propionyl]oxy]ethylcarbamate; $n_D^{20}$ 1.5003.

The D-starting material required for the manufacture of methyl 2-[[D-2-[p-[(6-chloro-2-quinoxalinyl)oxy]phenoxy]propionyl]oxy]ethylcarbamate can be obtained as follows:

2.0 g of D-2-(4-hydroxyphenoxy)propionic acid are heated at reflux for 1.5 hours with 13.1 g of thionyl chloride. The excess thionyl chloride is then distilled off and the residue is dried in a high vacuum. The thus-obtained acid chloride is taken up with 20 ml of methyl chloride and treated with 1.3 g of pyridine. A solution of 1.31 g of methyl 2-hydroxyethylcarbamate in 20 ml of methylene chloride is then added dropwise at 0°–5° C. during 15 minutes and the mixture is left to react at room temperature overnight. For the working-up, the mixture is concentrated on a rotary evaporator and then poured on to ice-water. The mixture is extracted twice with ethyl acetate and the extracts are washed with water and sodium chloride solution. The crude product obtained after drying over sodium sulphate and evaporation is purified by chromatography on silica gel. There is obtained methyl 2-[[D-2-(4-hydroxyphenoxy)-propionyl]oxy]ethylcarbamate $n_D^{20}$ 1.5201.

The 2,6-dichloroquinoxaline used above as the starting material can be obtained as follows:

1.44 g of sodium hydride (98%) are placed in 10 ml of dimethyl sulphoxide. A solution of 10.4 g of 4-chloro-2-nitroaniline in 40 ml of dimethyl sulphoxide is added dropwise in such a manner that the temperature does not rise above 30° C. After completion of the addition, the mixture is stirred for a further 30 minutes and then 13.25 g of ethyl diethoxyacetate are added rapidly. The mixture is stirred at room temperature overnight, then poured into 150 ml of water and extracted with ethyl acetate. The extracts are back-washed with water, dried and evaporated. The residue is recrystallized from ethanol/water. There is obtained 4-chloro-2,2-diethoxy-2'-nitroacetanilide of melting point 74°–76° C.

In an analogous manner, from 4-fluoro-2-nitroaniline there is obtained 4'-fluoro-2,2-diethoxy-2'-nitroacetanilide of melting point 78°–81° C.

0.8 g of Raney-nickel are placed in a hydrogenation flask and suspended in 50 ml of ethanol. 7.6 g of 4'-chloro-2,2'-diethoxy-2'-nitroacetanilide are added thereto and the mixture is hydrogenated at room temperature and normal pressure. The uptake of hydrogen has finished after 2 hours. After suction filtration and concentration of the filtrate, the product is precipitated with water. There is obtained 4'-chloro-2,2-diethoxy-2'-aminoacetanilide of melting point 89°–90° C.

In an analogous manner, from 4'-fluoro-2,2-diethoxy-2'-nitroacetanilide there is obtained 4'-fluoro-2,2-diethoxy-2'-aminoacetanilide of melting point 51°–53° C.

136 g of 4'-chloro-2,2-diethoxy-2'-aminoacetanilide are dissolved in 2000 ml of ethanol and the solution is then diluted with 630 ml of water. After the addition of 132 g of Amberlyst 15 (Fluka 66423), the mixture is stirred at reflux temperature for 4 hours. The mixture is filtered while hot in order to remove the Amberlyst. The solution is cooled to 0° C. and the crystallized-out product is filtered off. The mother liquor is concentrated, further crystals being again filtered off.

The product, yellow to beige crystals, is dried at 80° C. under reduced pressure. The 2-hydroxy-6-chloroquinoxaline obtained melts at 323° C.

In an analogous manner, from 4'-fluoro-2,2-diethoxy-2'-aminoacetatanilide there is obtained 2-hydroxy-6-fluoroquinoxaline of melting point 304°–305° C.

45 g of 2-hydroxy-6-chloroquinoxaline are treated in a sulphonation flask with 100 ml of phosphorus oxychloride. The mixture is stirred at reflux temperature for 20 minutes. The excess phosphorus oxychloride is thereupon distilled off and the residue is treated with 500 ml of ice-water. The product obtained is filtered off and washed with water until it is neutral. By crystallization from ethanol/water there is obtained 2,6-dichloroquinoxaline of melting point 152° C.

In an analogous manner, from 2-hydroxy-6-fluoroquinoxaline there is obtained 2-chloro-6-fluoroquinoxaline, m.p. 152° C.

II. FORMULATION EXAMPLES

Example 3

For the manufacture of an emulsifiable concentrate the ingredients listed hereinafter are mixed with one another:

| Emulsifiable concentrate 1 | |
|---|---|
| Active substance of formula I | 250 g |
| Castor oil-(20)-ethoxylate | 50 g |
| Calcium dodecylbenzene sulphonate | 25 g |
| Solvent mixture of ethylbenzenes | 150 g |
| N—Methyl-2-pyrrolidone | to 1000 ml |
| Emulsifiable concentrate 2 | |
| Active substance of formula I | 125 g |
| Castor oil-(20)-ethoxylate | 50 g |
| Calcium dodecylbenzene sulphonate | 25 g |
| N—Methyl-2-pyrrolidone | to 1000 ml |

The thus-obtained concentrate (1 or 2) emulsifies spontaneously in water and the resulting emulsion is suitable as a ready-for-use spray liquor.

Example 4

For the manufacture of a spray powder the ingredients listed hereinafter are mixed with one another and the mixture is thereupon finely ground:

| | |
|---|---|
| Active substance of formula I | 25 |
| Hydrated silicic acid | 5 |
| Alkylphenol-(12)-ethoxylate | 4 |
| Sodium polycarboxylate | 4 |

| | -continued |
|---|---|
| Siliceous earth | 62 |

The thus-obtained powder can be wetted with water. The resulting suspension is suitable as a ready-for-use spray liquor.

Example 5

For the manufacture of a dusting composition the ingredients listed hereinafter are mixed with one another and thereupon finely ground:

| | Weight percent |
|---|---|
| Active substance of formula I | 10 |
| Hydrated silicic acid | 7.5 |
| Talc | 82.5 |

Example 6

For the manufacture of a granulate the ingredients listed hereinafter are mixed with one another:

| | Weight percent |
|---|---|
| Active substance of formula I | 5 |
| Dipropylene glycol | 5 |
| Pumice stone granulate | 90 |

We claim:

1. A compound of the formula

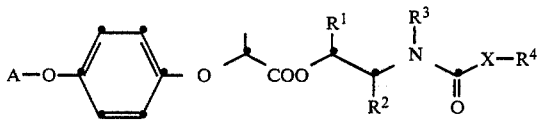

wherein A represents the group (a)

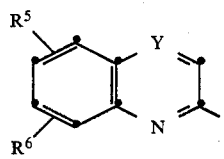

wherein $R^1$ is hydrogen, methyl or ethyl, $R^2$ is hydrogen, methyl or ethyl, $R^3$ is hydrogen or $C_{1-4}$-alkyl, $R^4$ is $C_{1-4}$-alkyl or halogen-substituted $C_{1-4}$-alkyl, $R^5$ is halogen, $C_{1-4}$-alkyl, halogen-substituted methyl, $C_{1-4}$-alkoxy or halogen-substituted methoxy, $R^6$ is hydrogen or chlorine, X is oxygen or sulfur and Y is nitrogen.

2. The compound according to claim 1, wherein $R^5$ is halogen, $C_{1-4}$-alkyl, trifluoromethyl, $C_{1-4}$-alkoxy, difluoromethoxy or trifluoromethoxy.

3. The method for combatting weeds which comprises applying to the locus to be protected, a herbicidally effective amount of a compound of claim 1.

4. The compound according to claim 2, wherein X is oxygen.

5. The compound according to claim 4, wherein $R^2$ and $R^3$ are hydrogen.

6. The compound according to claim 5, wherein $R^4$ is methyl or ethyl.

7. The compound according to claim 6, wherein $R^5$ is fluorine, chlorine or trifluoromethyl.

8. The compound according to claim 7, wherein $R^6$ is hydrogen.

9. A herbicidal compositon which comprises inert carrier material and, as the active ingredient, an amount of one or more of the compounds of claim 1 which is effective as a herbicide.

10. The compound according to claim 1 which is methyl 2-[[2-[p-[(6-chloro-2-quinoxalinyl)oxy]phenoxy]propionyl]oxy]ethylcarbamate.

11. The compound according to claim 1 which is methyl 2-[[2-[p-[(6-chloro-2-quinoxalinyl)]oxy]phenoxy]propionyl]oxy]propylcarbamate.

12. The compound according to claim 1 in D-form.

13. A compound according to claim 1 selected from the group consisting of from methyl 2-[[D-2-[p-[(6-chloro-2-quinoxalinyl)oxy]phenoxy]propionyl]oxy]-N-methyl-ethylcarbamate, ethyl 2-[[D-2-[p-[(6-chloro-2-quinoxalinyl)oxy]phenoxy]propionl]oxy]1-(ethyl)ethyl-carbamate, isobutyl 2-[[D-2-[p-[(6-chloro-2-quinoxalinyl)oxy]phenoxy]propionyl]oxy]ethylcarbamate, ethyl 2-[[D-2-[p-[(6-fluoro-2-quinoxalinyl)oxy]phenoxy]propionyl]oxy]ethylcarbamate and methyl 2-[[D-2-[p-[(6-fluoro-2-quinoxalinyl)oxy]phenoxy]propionyl]oxy]-propylcarbamate.

14. A herbicidal composition according to claim 9, comprising a compound in which $R^5$ is halogen, $C_{1-4}$-alkyl, trifluoromethyl, $C_{1-4}$-alkoxy, difluoromethoxy or trifluoromethoxy.

15. A method for combatting weeds which comprises applying to the locus to be protected, a herbicidally effective amount of the composition of claim 14.

16. A herbicidal composition which comprises inert carrier material and, as the active ingredient, an amount of one or more of the compounds of claim 10 which is effective as a herbicide.

17. A herbicidal composition which comprises inert carrier material and, as the active ingredient, an amount of one or more of the compounds of claim 11 which is effective as a herbicide.

18. A herbicidal composition which comprises inert carrier material and, as the active ingredient, an amount of one or more of the compounds of claim 13 which is effective as a herbicide.

19. A method for combatting weeds which comprises applying to the locus to be protected, a herbicidally effective amount of a composition of claim 9.

20. The method for combatting weeds which comprises applying to the locus to be protected, a herbicidally effective amount of the composition of claim 16.

21. A method for combatting weeds which comprises applying to the locus to be protected, a herbicidally effective amount of a composition of claim 17.

22. A method for combatting weeds which comprises applying to the locus to be protected, a herbicidally effective amount of the composition of claim 18.

* * * * *